United States Patent [19]
Berenson

[11] 3,931,406
[45] Jan. 6, 1976

[54] PYRAZOLIDINE FUNGICIDES
[75] Inventor: Herman Berenson, Trenton, N.J.
[73] Assignee: American Cyanamid Company, Stamford, Conn.
[22] Filed: Feb. 3, 1975
[21] Appl. No.: 546,480

[52] U.S. Cl............................ 424/273; 260/310 D
[51] Int. Cl.$^2$........................................ A01N 9/22
[58] Field of Search..................................... 424/273

[56] References Cited
UNITED STATES PATENTS
3,818,096   6/1974   Sherlock............................ 424/273

OTHER PUBLICATIONS
Chemical Abstracts, 70:96695Z (1969) and 16:6343S of 1967–1971 Subject Index.

Primary Examiner—Leonard Schenkman
Attorney, Agent, or Firm—Harry H. Kline

[57] ABSTRACT
There is provided a method for protecting plants from attack by fungi by applying to said plants a fungicidally effective amount of a pyrazolidine and acid salt derivatives thereof.

11 Claims, No Drawings

PYRAZOLIDINE FUNGICIDES

The present invention relates to the use of pyrazolidine compounds and the acid salts thereof as antifungal agents. These antifungal compounds are represented by the formula:

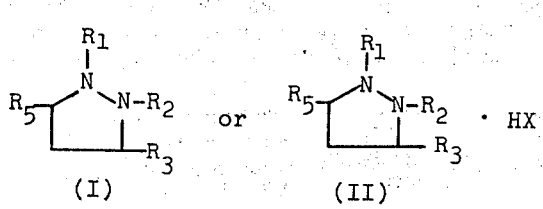

wherein $R_1$ and $R_2$ each represent alkyl $C_1$–$C_4$; $R_3$ and $R_5$ each independently represent members selected from the group consisting of cycloalkyl $C_3$–$C_7$ and

Y represents a member selected from the group consisting of hydrogen, halogen and alkyl $C_1$–$C_4$; and HX represents an acid, preferably selected from the group consisting of HCl, HBr, HI, $HNO_3$, $H_3PO_4$, $H_2SO_4$, $HClO_4$ and

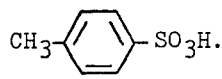

Preferred pyrazolidine compounds, for use in the method of the present invention, are depicted by formulas (I) and (II) above, wherein $R_1$ and $R_2$ are each methyl, $R_3$ and $R_5$ are each independently selected from the group consisting of cyclohexyl and

Y represents a member selected from the group consisting of hydrogen, halogen and methyl; and HX is an inorganic acid selected from those mentioned above.

Another preferred embodiment of this invention relates to the use of pyrazolidine compounds depicted by formulas (I) and (II) above, for the protection of living plants, said compounds have the formula as shown above wherein $R_1$ and $R_2$ are each methyl; $R_3$ is phenyl, o-, m- or p-fluorophenyl, or o-, m- or p-methylphenyl, $R_5$ is phenyl, o-, m- or p-fluorophenyl, or o-, m- or p-methylphenyl; and in formula (II) compounds, HX is HI, HCl, HBr, $HNO_3$ or $H_2SO_4$.

The above-identified pyrazolidine compounds, which are represented by formulas (I) and (II), can be prepared as the "cis" and the "trans" isomers. Both isomeric forms of the compounds are biologically active, however, the "cis" isomers are the more active of the two. Mixed isomer compositions are, of course, also biologically active.

The term "halogen" as used herein is intended to mean fluoro, chloro, bromo and iodo, however fluoro is preferable.

Although, at first glance, the pyrazolidines and pyrazolidine salts of this invention may appear, to one who is not skilled in the art, to be similar to pyrazolium and pyrazolinium compounds, it must be recognized that these latter-named compounds are quaternary salts, and thus, such ionic compounds are generally water soluble. The pyrazolidines (I) are not salts, nor are they quaternary compounds, and they are water-insoluble materials. The pyrazolidine (II) compounds are, of course, salts; however, like the pyrazolidines (I), they are not quaternary compounds.

Quaternary compounds are obtained with a positive charge on the nitrogen and a carbon atom attached to the nitrogen; whereas, the salt is obtained by protonation of the nitrogen which may or may not have an alkyl group attached. A salt and a quaternary may be illustrated as follows:

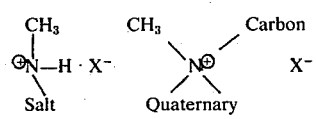

Additionally, the action of base on an HX salt of an amine will regenerate the amine, i.e. a pyrazolidine, whereas, base upon a pyrazolium compound merely changes the counterion $X^-$ to $OH^-$.

The pyrazolidines (I) are nonionic, lipophilic molecules which are found to be effective as foliar fungicides, especially effective for the control of powdery mildew on a variety of plant species, especially cereal grains such as barley, wheat, corn or sorghum.

The pyrazolidines of this invention can be prepared by a reductive process. Pyrazolium compounds (III), below, can be reduced in high yield (by Method A) in protonic solvents with an excess of sodium borohydride, between room temperature and reflux temperature of the solvent, e.g. in isopropanol (80°C) or other lower alcohol $C_1$–$C_4$. Other reducing agents may be substituted, e.g., lithium aluminum hydride and an ether such as tetrahydrofuran (THF) or diethyl ether. This reduction probably involves the intermediacy of a Δ-3-pyrazoline. Milder conditions (e.g., room temperature) are employed for the reduction of 2-pyrazolinium compounds to pyrazolidines, shown hereinafter as Method B. The pyrazolidines are readily separated from any unreacted starting material by virtue of their solubility in aprotic solvents such as benzene, ethers or chlorinated hydrocarbons. Most of the pyrazolidines so obtained are oils, which are shown by gas liquid chromatography (glc) and nuclear magnetic resonance (nmr) to be isomer mixtures generally in the range of cis:trans 80:20. Further characterization of the pyrazolidines is obtained by conversion to a salt using an aqueous acid, e.g., HCl or HI. In some cases, the salt precipitates out such as with perchloric or hydriodic acid, and the product is removed by filtration. Sometimes an oil results, which with manipulation readily affords a solid. In some cases, the salt is extracted from the aqueous acidic medium (e.g., aqueous HCl) with chloroform, which upon evaporation affords the salt. Alternatively, hydrochlorides can be prepared by passing dry hydrogen chloride gas through an aprotic solvent such as an ethereal solution of the pyrazolidine, from which the hydrochloride salt precipitates out and is removed by filtration.

Separation of cis and trans pyrazolidines is achieved preparatively by dry column chromatography using Woelm Silica Gel, prepared for dry chromatography as the packing, and hexane-ether (80:20) as the eluant. The "trans" isomer runs somewhat faster than the "cis" isomer, which is the basis for the separation. The separation is confirmed by glc using a mixed phase column, 3% SP-2250, 3.95% SP-2401 column at 175°C and by nmr (CDCl$_3$) spectra.

Alternatively, the pyrazolidines I can be obtained from chalcones by successive reaction with hydrazines, followed by reduction, as described above, or reductive alkylation. The reaction may be graphically illustrated as follows:

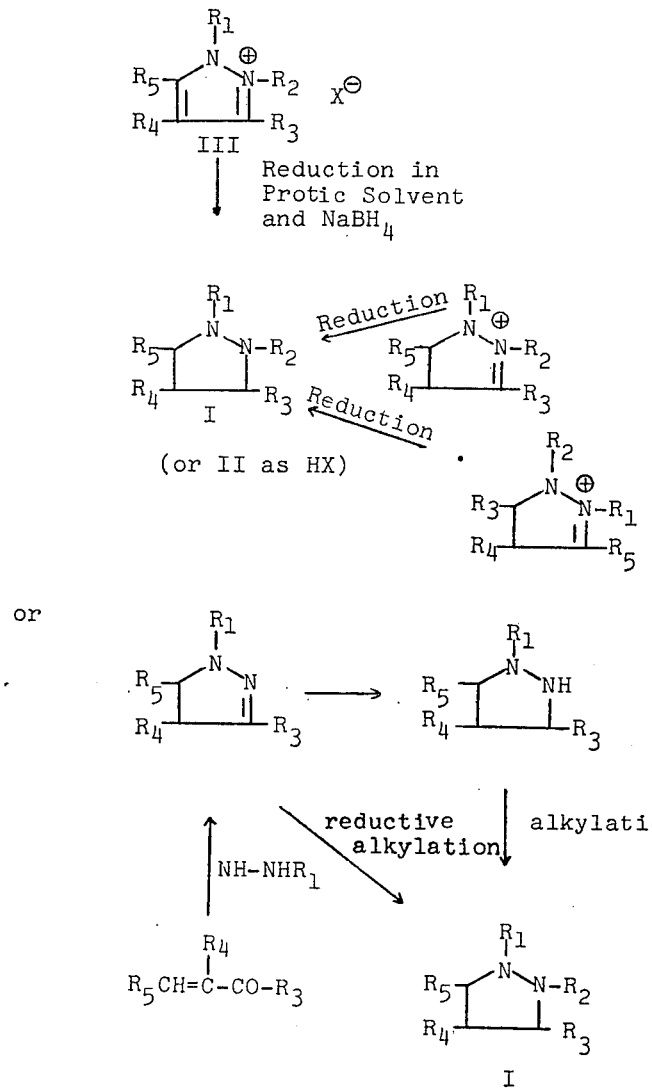

material to the foliage of the plant in the form of a liquid, preferably aqueous, spray. Solutions or suspensions containing from about 50 to 5,600 ppm, and preferably 100 to 500 ppm of the pyrazolidine cation or free base are generally highly effective for this use.

As the pyrazolidine salts (II) of this invention exhibit good water solubility, the active salts can simply be dissolved in water and applied to the plants as such, or a surfactant or mixture of surfactants can be added either to the formulation or to the aqueous mixture to be applied.

The pyrazolidines and pyrazolidine salts, I and II respectively, can be prepared as wettable powders, emulsifiable concentrates or as water miscible concentrates which are diluted with water or other suitable polar solvent, and then applied as a dilute aqueous spray. Generally, such sprays are applied at the volume rate of about 938 to 1877 l/ha or about 100 to 200 gal per acre. It is, of course, obvious that smaller or larger volumes of liuqid spray may be employed, e.g., 400 to 4,000 l/ha may be used depending on a variety of factors including the type of crop, the plant spacing and the amount of foliage per plant being treated. It is also obvious that the preferred concentration may vary when the volume of spray varies.

While fungicide treatments are generally discussed in terms of concentration of active ingredient in ppm in As previously stated, it has been found that the compound of this invention are useful for the control of fungi which infect many living plants. They are particularly effective for controlling powdery mildew, especially on grains such as barley and wheat, on vines such as cucumbers, grapes and pumpkin and on fruit and nut trees such as apples, pears and pecans. They are also effective for controlling fungi which are the causative agents for diseases such as rice blast, and apple scab and can be used to protect ornamentals and shrubs.

In utilizing the above-identified pyrazolidine compounds for protecting plants from pathogenic fungi, I have found it most advantageous to apply the active the solution or suspension, it should also be noted that, with the compounds of the present invention, it is generally desirable to apply the pyrazolidine or pyrazolidine salt in an amount sufficient to provide about 0.056 to 11.8 kg/ha and preferably 0.56 to 4.48 kg/ha of said compound.

Wettable powder formulations can be prepared by grinding together about 25% to 95% by weight of the pyrazolidine or pyrazolidine salt and about 75% to 5% by weight of a solid diluent such as attapulgite, kaolin, bentonite, diatomaceous earth, silica, talc, fullers earth or the like. To this mixture is added about 1% to 5% by weight of a dispersing agent such as the calcium salt of a polymerized alkyl aryl sulfonic acid, sodium lignosulfonate, or sodium salt of condensed naphthalene sulfonic acid and about 1% to 5% by weight of a surfactant, such as polyoxyethylated vegetable oil, alkyl phenoxy polyoxyethylene ethanol, sodium alkyl naphthalene sulfonate is also blended with the formulation.

The emulsifiable concentrate formulations can be prepared by dissolving about 25% to 75% by weight of the pyrazolidine free base in an aromatic solvent such as xylene, toluene or benzene, and adding thereto about 5% to 10% by weight of a nonionic, anionic or nonionic-anionic emulsifier. The thus-prepared formulation is then readily dispersible in water and can be applied as a dilute spray.

The water-miscible concentrates are prepared by dissolving from 15% to 70% by weight of the compound, preferably the pyrazolidine salt, in 85% to 30% by weight of a water-miscible solvent, such as 2-methoxy ethanol, methanol, propylene glycol, diethylene glycol, diethylene glycol monoethyl ether, formamide, and methylformamide. Application of the material is generally made by adding a predetermined quantity of the water-miscible concentrate to a spray tank and adding thereto a quantity of water sufficient to provide the desired concentration of active ingredient in solution, and spraying the thus prepared solution on the foliage of plants which are to be protected.

The performance of the product in the above formulations, which are applied as liquid sprays, is improved by adding a surfactant or blend of surfactants thereto. Conventional nonionic surfactants are preferred and the surfactants are preferably added to the formulation itself or the spray tank to give a final finished spray containing 0.1% to 5% by volume to provide good wetting of the spray solution on plant foliage.

Suitable nonionic surfactants include alkyl polyoxyethylene ethers, polyoxyethylene (20) sorbitan monolaurate, polyoxyethylene (20) sorbitan monooleate, alkylarylpolyglcol ethers, alkyl phenol ethoxylates, trimethyl nonyl polyethylene glycol ethers, alkyl phenol ethylene oxide condensates, octyl phenoxy polyethoxy ethanols, nonylphenyl polyethylene glycol ethers, condensates of polyoxy ethylenes, polyoxy propylenes, aliphatic polyethers, aliphatic polyesters, alkaryl polyoxyethylene glycols, and the like. Especially preferred nonionic surfactants having a hydrophilic-lipophilic balance (HLB) of from 11 to 16. This conventional surfactant classification test is described, for example, at page 232 et seq of *Emulsion Theory and Practice* by Paul Becker, Rheinholt Publishing Corporation, Second Edition (1965); also available as No. 162 in the American Chemical Society's Monograph Series.

Preferred methods employ water as the diluent and the 1,2-dimethyl-3,5-diphenylpyrazolidine or acid salt thereof or the 1,2-dimethyl-5-phenyl-3-fluorophenyl-pyrazolidine or pyrazolidine acid salt as the active ingredient.

This invention is further illustrated by the examples set forth below which are provided simply by way of illustration.

EXAMPLE 1

The fungicidal activity of the compounds of the present invention is demonstrated in the following tests.

Plants (barley and wheat) are individually grown in 5.08 cm peat squares and assembled in fibre containers the week prior to spraying.

Spray solutions are prepared at final concentrations of 100 ppm and/or 500 ppm in 50/50 acetone/water mixtures. The plants are placed on a turntable and sprayed with 50 ml of test solution. Immediately thereafter they are placed on greenhouse benches and permitted to dry. After drying, said treated plants are dusted with powdery mildew spores and the dusted plants are then placed in a constant temperature room (22°C, 12 hours light and 45% RH) for from 7 to 9 days to await disease expression. At the end of the holding period, all plants are examined and rated according to the performance rating system provided below.

Performance Rating

All plants are rated for disease severity on a scale of 1 to 7 (clean to kill), as described below:

| Rating | Description |
| --- | --- |
| 1 | Nil |
| 2 | Trace disease |
| 3 | Slight disease |
| 4 | Moderate disease |
| 5 | Heavy disease |
| 6 | Severe disease |
| 7 | Kill |

Data obtained are reported in Table I below.

Table I

| Control of Powdery Mildew on Barley and Wheat | | |
| --- | --- | --- |
| Compound | Rate ppm | Disease Severity Barley / Wheat |
| 1,2-Dimethyl-3,5-diphenylpyrazolidine hydrochloride* | 500 / 100 | 1 / 1 — 2 / 2 |
| 1,2-Dimethyl-3,5-diphenylpyrazolidine perchlorate* | 500 | 1 / 1 |
| 1,2-Dimethyl-3,5-diphenylpyrazolidine nitrate* | 500 | 1 / 1 |
| 1,2-Dimethyl-3,5-diphenylpyrazolidine hydrobromide* | 500 / 100 | 1 / 1 — 1 / 2 |
| 3-(p-Fluorophenyl)-1,2-dimethyl-5-phenyl-pyrazolidine hydriodide* | 500 | 2 / 1 |
| 3-(p-Fluorophenyl)-1,2-dimethyl-5-phenyl-pyrazolidine* | 500 | 2 / 1 |
| 3-(o-Fluorophenyl)-1,2-dimethyl-5-phenyl-pyrazolidine hydriodide* | 500 | 1 / 1 |
| 3-(o-Fluorophenyl)-1,2-dimethyl-5-phenyl-pyrazolidine* | 500 | 1 / 1 |

EXAMPLE 2

To determine the effectiveness of pyrazolidine compound as fungicidal agents a variety of pathogenic fungi, host plants and pyrazolidine and pyrazolidine acid salts are used in the following tests. Pathogens, host plants, the method of testing and the rating system used are reported below along with the data obtained.

Pathogens:
  Piricularia oryzae Cavara, the rice blast pathogen.
  Venturia inaequalis (Cke.) Wint. which causes apple scab.
  Erysiphe cichoracearum DC, the cause of powdery mildew on cucurbits.
  Podosphaera leucotricha (E. & E.) Salm., the cause of powdery mildew of apples and pears.
  Erysiphe graminis f. sp. tritci the cause of powdery mildew on wheat.
  Erysiphe graminis f. sp. hordei the cause of powdery mildew on barley.

Host Plants:
  Rice (Oryza sativa) Cv. Nato)
  Cucumber (Cucumis sativus) (Cv. Marketer)
  Apple (Malus sylvestris) (Seedling)
  Wheat (Triticum aestivum Cv. Bonanza)
  Barley (Hordeum vulgare Cv. Larker)

Plants are individually grown in 5.08 cm peat squares and assembled in 7.62 cm × 25.4 cm pressed fibre containers the week prior to spraying. With the exception of rice and wheat, a single specimen of each species is used. A separate container is used for those plants in the mildew evaluation. The complete test system is shown below.

| Series 1 | Series 2 |
|---|---|
| Rice: Rice Blast | Apple: Powdery Mildew |
| Apple: Apple Scab | Cucumber: Powdery Mildew |
| | Wheat: Powdery Mildew |
| | Barley: Powdery Mildew |

Spray solutions are prepared at a final concentration of 100 or 500 ppm in 50 ml of 50% aqueous acetone. In all cases, acetone is added first to solubilize the compound and solutions made to final volume with deionized water.

Two containers, one each from Series 1 and 2 (see above), are sprayed simultaneously on a turntable with 50 ml of the test solution. Spray is provided by 2 fixed Spraying System Co. nozzles mounted to deliver vertical and horizontal solid cone spray patterns. Immediately thereafter, all plants, are returned to the greenhouse to permit the deposit to dry.

Plants of Series 1 and 2 are separately inoculated. Plants in Series 1 are inoculated with conidial suspensions of the respective pathogens using a DeVilbiss paint sprayer operated at 4–6 psig and immediately transferred to a controlled temperature/humidity cabinet (ambient temperature RH 95%). Plants in Series 2 are dusted with respective powdery mildew conidia and then, with the exception of apple seedlings, removed to the constant temperature room previously described to await disease development. Apple seedlings are transferred to the greenhouse to await disease expression. Plants in Series 1 are held 4 days in the cabinet then transferred to the greenhouse to await disease expression.

All plants are rated for disease severity on a scale of 1–7 (clean-kill), as described in Example 1 above.

In the accompanying tables a rating for acceptable control and a rating for the controls or checks is given.

Data are reported for the minimum effective level tested and where tests are repeated average values are reported. Ratings for controls are averages from two or more tests.

Table II

Antifungal Activity of Pyrazolidine* and Pyrazolidine Acid Salts*

| Compound | Mean Disease Severity at Indicated Spray rates, ppm | | | |
|---|---|---|---|---|
| | Rice Blast | | Apple Scab | |
| | 500 ppm | 100 ppm | 500 ppm | 100 ppm |
| Acceptable Disease Control Level | 1–3 | | 1–3 | |
| Controls | 4.8 | | 5.6 | |
| cis-1,2-Dimethyl-3,5-diphenylpyrazolidine | | | 3.0 | |
| trans-1,2-Dimethyl-3,5-diphenylpyrazolidine hydrochloride | | | 3.0 | |
| cis-1,2-Dimethyl-3,5-diphenylpyrazolidine hydrochloride | | | 2.0 | |
| 3,5-Dicyclohexyl-1,2-dimethylpyrazolidine perchlorate | | | 2.0 | |
| 3-(p-Fluorophenyl)-1,2-dimethyl-5-phenyl-pyrazolidine | 3.0 | 3.0 | | |
| 1,2-Dimethyl-3-(o-tolyl)-5-(p-tolyl)pyrazolidine hydriodide | 3.5 | 2.0 | | |
| 1,2-Dimethyl-3-(o-tolyl)-5-(p-tolyl)pyrazolidine | 3.0 | 3.0 | | |
| 1,2-Dimethyl-3,5-di-o-tolylpyrazolidine hydriodide | | | 3.0 | 1.0 |
| 3-(o-Fluorophenyl)-1,2-dimethyl-5-phenyl-pyrazolidine hydriodide | | | 3.0 | |

*All compounds are 80:20 cis-trans mixture unless otherwise specified

Table III

Antifungal Activity of Pyrazolidine* and Pyrazolidine Acid Salts*

| Compound | Mean Disease Severity at Indicated Spray Rates, ppm | | | | | | | |
|---|---|---|---|---|---|---|---|---|
| | CUC Powdery | | Wheat Powdery | | Apple Powdery | | Barley Powdery | |
| | 500 | 100 | 500 | 100 | 500 | 100 | 500 | 100 |
| Acceptable Disease Control Level | 1–3 | | 1–3 | | 1–3 | | 1–3 | |
| Controls | 5.9 | | 5.1 | | 5.5 | | 6.0 | |
| 1,2-Dimethyl-3,5-diphenylpyrazolidine hydrochloride | | | 1.5 | 2.0 | | | 1.5 | 2.0 |
| trans-1,2-Dimethyl-3,5-diphenylpyrazolidine | | | 2.0 | | 2.0 | | | |
| cis-1,2-Dimethyl-3,5-diphenylpyrazolidine | 3.0 | | 2.0 | | 3.0 | | | |

Table III-continued

Antifungal Activity of Pyrazolidine* and Pyrazolidine Acid Salts*

Mean Disease Severity at Indicated Spray Rates, ppm

| Compound | CUC Powdery 500 | CUC Powdery 100 | Wheat Powdery 500 | Wheat Powdery 100 | Apple Powdery 500 | Apple Powdery 100 | Barley Powdery 500 | Barley Powdery 100 |
|---|---|---|---|---|---|---|---|---|
| Acceptable Disease Control Level | | | 1–3 | | 1–3 | | 1–3 | 1–3 |
| Controls | | | 5.9 | | 5.1 | | 5.5 | 6.0 |
| trans-1,2-Dimethyl-3,5-diphenylpyrazolidine hydrochloride | | | 2.0 | | | | | |
| cis-1,2-Dimethyl-3,5-diphenylpyrazolidine hydrochloride | | | 1.0 | | 3.0 | | 1.0 | 1.0 |
| 1,2-Dimethyl-3,5-diphenylpyrazolidine perchlorate | | | 1.5 | | 3.0 | | 1.0 | 3.0 |
| 3-(p-Fluorophenyl)-1,2-dimethyl-5-phenyl-pyrazolidine hydriodide | | | 2.3 | | | | 1.0 | |
| 3-(p-Fluorophenyl)-1,2-dimethyl-5-phenyl-pyrazolidine | | | 2.0 | | | | 1.0 | |
| 1,2-Dimethyl-3-(o-tolyl)-5-(p-tolyl)pyra-zolidine hydriodide | | | 1.0$^m$ | | 3.0 | | | |
| 1,2-Dimethyl-3-(o-tolyl)-5-(p-tolyl)pyra-zolidine | | | 1.0$^m$ | | 3.0 | | | |
| 1,2-Dimethyl-3,5-di-o-tolylpyrazolidine hydriodide | | | 3.0 | | | | | |
| 1,2-Dimethyl-3,5-di-m-tolylpyrazolidine hydriodide | 1.0$^m$ | 3.0 | 1.0 | 2.0 | | | 1.0 | 2.0 |
| 3-(o-Fluorophenyl)-1,2-dimethyl-5-phenylpyrazolidine | | | 2.0 | 3.0 | | | 1.0 | |
| 1,2-Dimethyl-3,5-diphenylpyrazolidine nitrate | | | 1.0 | | | | 1.0 | |
| 1,2-Dimethyl-3,5-diphenylpyrazolidine hydrobromide | | | 1.0 | 1.0 | | | 1.0 | 2.0 |
| 3-(o-Fluorophenyl)-1,2-dimethyl-5-phenylpyrazolidine hydriodide | | | 1.5 | 3.0 | | | | |

*All compounds are 80:20 cis-trans mixture unless otherwise specified
m=Moderate phytotoxicity

EXAMPLE 3

Preparation of 1,2-Dimethyl-3,5-diphenylpyrazolidine (Method A).

Sodium borohydride (19 g, 0.5 mole) is added portionwise to an isopropanol (1 l) solution of 1,2-dimethyl-3,5-diphenylpyrazolium methyl sulfate (40.1 g, 0.25 mole). The reaction is allowed to stir at room temperature for 3 days; then additional sodium borohydride (9 g, 0.25 mole) is added, and the reaction is heated to reflux with stirring and maintained there for 7 hours. The reaction mixture is cooled to room temperature and water (100 ml) is added over a 1½-hour period. After stirring for 2 hours, the isopropanol is removed on a rotary evaporator, and the resulting paste slurried in water and extracted with diethyl ether. Evaporation of the ether layer gives the pyrazolidine as a viscous oil; 48.3 g, 72%, which is characterized by nmr, ir, glc and analyzed as its HCl salt.

Analyses calculated for $C_{17}H_{21}N_2Cl$: C, 70.70; H, 7.33; N, 9.70. Found: C, 70.59; H, 7.49; N, 9.44.

Compounds in Table I, designated by Method A, are prepared in a similar manner, from pyrazolium quaternary salts and sodium borohydride.

EXAMPLE 4

Preparation of 1,2-Dimethyl-3-(m-fluorophenyl)-5-phenyl-pyrazolidine hydriodide (Method B).

Sodium borohydride (76 g, 0.02 mole) is added to a slurry of 1,2-dimethyl-3-(m-fluorophenyl)-5-phenyl-pyrazolinium iodide (4 g, 0.01 mole) in isopropanol (125 ml). After becoming homogeneous, the reaction mixture is stirred for 24 hours; then water (10 ml) is carefully added. The alcohol is removed on a rotary evaporator, and the residue slurried in water (50 ml) and extracted with chloroform. Evaporation of the organic layer gives an oil, which is slurried in water, and aqueous hydriodic acid (5 ml, 46–50%) is added. After stirring for one hour, the resulting solid is filtered and dried to give 3.3 g, 83%; melting point 187°–189°C.

Analyses calculated for $C_{17}H_{20}N_2FI$: C, 51.27; H, 5.06; N, 7.03. Found: C, 51.59; H, 5.25; N, 7.10.

Compounds prepared by Method B are also listed in Table IV, and are prepared in a similar manner to the above example by reduction of pyrazolinium salts with sodium borohydride.

EXAMPLE 5

Separation of Isomers

The isomer mixture of 1,2-dimethyl-3,5-diphenyl-pyrazolidine (50 g, 80:20 cis:trans) is taken up in a hexane-ether (80:20) mixture, and passed through a "dry" silica gel column 5 feet in length and 2½ inches in diameter with the same solvent system. The fractions are cut off, stripped off the silica gel with methanol, the methanol removed by evaporation and the residue azeotropically dried with toluene to give:

1. $F_3$ — faster moving trans-isomer 95% (glc, 175°C, mixed phase column 3% SP-2250, 3.95% SP-2401). Analyses calculated for $C_{17}H_{20}N_2$: C, 80.91; H, 7.99; N, 11.10. Found: C, 80.92; H, 8.29; N, 10.91; anad and 2. $F_{5,6,7}$ — slower cis-isomer 97% (glc as above). Analyses calculated for $C_{17}H_{20}N_2$: C, 80.91; H, 7.99; N, 11.10. Found: C, 80.52; H, 8.07; N, 10.90.

The hydrochlorides of both are prepared, as exemplified by the following.

Aqueous hydrochloric acid (4 ml) is added to a water suspension of the cis-isomer (5.0 g) and the reaction mixture stirred for ½ hour. The mixture is extracted with chloroform, and the organic layer concentrated to an oil and azeotropically dried with toluene. The oil is taken up in chloroform (50 ml), and a solid precipitates out upon addition of ether and is filtered and dried to give 3.7 g, 65%; melting point 194°–195°C.

Analyses calculated for $C_{17}H_{21}N_2Cl$: C, 70.70; H, 7.33; N, 9.70. Found: C, 70.93; H, 7.48; N, 9.78.

EXAMPLE 6

Following the procedure of Examples 1 or 2 above but employing the appropriate 1,2-dialkyl-3,5-diphenylpyrazolium compound yields the compounds listed below in Table IV.

Table IV

| Compound | Preparation of Pyrazolidine Compounds Melting Point °C | Method Example No. |
| --- | --- | --- |
| 1,2-Dimethyl-3,5-diphenylpyrazolidine hydrochloride | 190–192 | 1 |
| 1,2-Dimethyl-3,5-diphenylpyrazolidine | oil | 1 |
| Trans-1,2-dimethyl-3,5-diphenylpyrazolidine | oil | 1 |
| Cis-1,2-dimethyl-3,5-diphenylpyrazolidine | oil | 1 |
| Trans-1,2-dimethyl-3,5-diphenylpyrazolidine hydrochloride | 152–154 | 1 |
| Cis-1,2-dimethyl-3,5-diphenylpyrazolidine hydrochloride | 194–195 | 1 |
| 3,5-Dicyclohexyl-1,2-dimethylpyrazolidine perchlorate | 146–148 | 1 |
| 3,5-Dicyclohexyl-1,2-dimethylpyrazolidine | oil | 1 |
| 1,2-Dimethyl-3,5-diphenylpyrazolidine hydriodide | 195–196 | 1 |
| 1,2-Dimethyl-3,5-diphenylpyrazolidine nitrate | 72–74 | 1 |
| 1,2-Dimethyl-3,5-diphenylpyrazolidine perchlorate | 138 | 1 |
| 1,2-Dimethyl-3,5-diphenylpyrazolidine hydrobromide | 196–199 | 1 |
| 1,2-Dimethyl-3,5-diphenylpyrazolidine p-toluene sulfate | Viscous glass | 1 |
| 1,2-Dimethyl-3,5-diphenylpyrazolidine hydrogen sulfate | 94 | 1 |
| 3-(p-Fluorophenyl)-1,2-dimethyl-5-phenylpyrazolidine hydriodide | 195–198 | 2 |
| 3-(p-Fluorophenyl)-1,2-dimethyl-5-phenylpyrazolidine | oil | 2 |
| 3-(o-Fluorophenyl)-1,2-dimethyl-5-phenylpyrazolidine | oil | 2 |
| 3-(o-Fluorophenyl)-1,2-dimethyl-5-phenylpyrazolidine hydriodide | 168–170 | 2 |
| 3-Cyclohexyl-1,2-dimethyl-5-phenylpyrazolidine hydriodide | 90 | 1 |
| 3-(m-Fluorophenyl)-1,2-dimethyl-5-phenylpyrazolidine hydriodide | 187–189 | 2 |
| 3-(p-Chlorophenyl)-1,2-dimethyl-5-phenylpyrazolidine hydriodide | 178 | 1 |
| 1,2-Dimethyl-3,5-di(m-tolyl)pyrazolidine hydriodide | 182–185 | 2 |
| 1,2-Dimethyl-3,5-di(o-tolyl)pyrazolidine hydriodide | 212–219 | 2 |
| 1,2-Dimethyl-3-(o-tolyl)-5-(p-tolyl)pyrazolidine hydriodide | 167–168 | 2 |
| 1,2-Dimethyl-3-(o-tolyl)-5-(p-tolyl)pyrazolidine | oil | 1 |

I claim:

1. A method for protecting growing plants from attack by fungal organisms comprising applying to the foliage of said plants a fungicidally effective amount of a compound having a formula selected from the group consisting of:

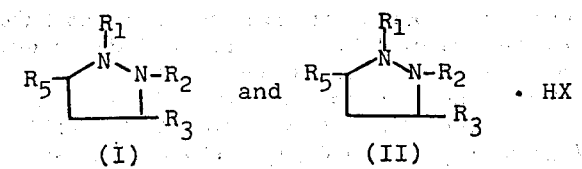

wherein $R_1$ and $R_2$ each represent alkyl $C_1$–$C_4$; $R_3$ and $R_5$ each represent a member selected from the group consisting of cycloalkyl $C_3$–$C_7$; and

Y represents a member selected from the group consisting of hydrogen, halogen and alkyl $C_1$–$C_4$; and HX represents an acid.

2. The method according to claim 1, wherein HX represents an acid selected from the group consisting of HCl, HBr, HI, $HNO_3$, $H_3PO_4$, $H_2SO_4$, $HClO_4$ and

3. The method according to claim 1, wherein $R_1$ and $R_2$ are methyl; $R_3$ and $R_5$ each represent a member selected from the group consisting of cyclohexyl and

Y represents a member selected from the group consisting of hydrogen, fluoro and methyl; and HX is an inorganic acid.

4. The method according to claim 1, wherein the fungal organism causes powdery mildew, and the plant to be protected is barley or wheat.

5. The method according to claim 1, wherein the compound is cis-1,2-dimethyl-3,5-diphenylpyrazolidine hydrochloride.

6. The method according to claim 1 wherein the compound is 1,2-dimethyl-3,5-di-m-tolylpyrazolidine hydroiodide.

7. The method according to claim 1 wherein the compound is 1,2-dimethyl-3,5-diphenylpyrazolidine hydrobromide.

8. The method according to claim 1 wherein said compound is brought into contact with the foliage in the form of an aqueous spray containing 50 to 5,600 ppm of said compound.

9. The method according to claim 1 wherein said compound is in the cis form.

10. The method according to claim 1 wherein said compound is the free base.

11. The method according to claim 1 wherein said compound is the acid salt.

* * * * *